(12) United States Patent
Willeit et al.

(10) Patent No.: US 10,844,340 B2
(45) Date of Patent: Nov. 24, 2020

(54) LIQUID SUBSTRATE TANK FOR A BIOGAS PLANT

(71) Applicants: BTS BIOGAS SRL/GMBH, Bruneck (IT); Jan Willeit, Enneberg (IT)

(72) Inventors: Jan Willeit, Enneberg (IT); Michael Niederbacher, Bruneck (IT)

(73) Assignees: BTS BIOGAS SRL/GMBH, Bruneck (IT); Jan Willeit, Enneberg (IT)

( * ) Notice: Subject to any disclaimer, the term of this patent is extended or adjusted under 35 U.S.C. 154(b) by 686 days.

(21) Appl. No.: 15/501,929

(22) PCT Filed: Jul. 31, 2015

(86) PCT No.: PCT/EP2015/001579
§ 371 (c)(1),
(2) Date: Feb. 6, 2017

(87) PCT Pub. No.: WO2016/020049
PCT Pub. Date: Feb. 11, 2016

(65) Prior Publication Data
US 2017/0226461 A1    Aug. 10, 2017

(30) Foreign Application Priority Data
Aug. 4, 2014 (DE) .................. 10 2014 011 315

(51) Int. Cl.
*C12M 1/00* (2006.01)
*C12M 1/02* (2006.01)
(Continued)

(52) U.S. Cl.
CPC ............ *C12M 27/20* (2013.01); *C12M 21/04* (2013.01); *C12M 23/40* (2013.01); *C12M 27/00* (2013.01);
(Continued)

(58) Field of Classification Search
CPC ...... C12M 21/04; C12M 23/40; C12M 27/00; C12M 27/20; C12M 29/00; C12M 41/40; Y02E 50/343
See application file for complete search history.

(56) References Cited

U.S. PATENT DOCUMENTS

| 4,530,762 A | 7/1985 | Love |
| 8,759,083 B2 | 6/2014 | Lutz |

(Continued)

FOREIGN PATENT DOCUMENTS

| AU | 2008201899 A1 | 11/2008 |
| CN | 102321528 A | 1/2012 |

(Continued)

*Primary Examiner* — Gautam Prakash
*Assistant Examiner* — Lydia Edwards
(74) *Attorney, Agent, or Firm* — Laurence A. Greenberg; Werner H. Stemer; Ralph E. Locher

(57) ABSTRACT

A liquid substrate tank for a biogas plant includes an interior fillable with a liquid substrate and a bottom wall defining the interior on the bottom and being particularly at least regionally flat. A trough-shaped recess extending over a partial region of the bottom wall is formed in the bottom wall, to which and/or into which recess an extraction line of an extraction device is guided. The extraction device has an open-loop and/or closed-loop control device actuating the extraction device for extracting a substrate/sand mixture accumulating in the recess during operation from the recess and thus from the interior through the extraction line. The extraction device has an accommodation and/or sedimentation tank, or separator, connected to the extraction line relative to flow for accommodating or separating the substrate/sand mixture extracted through the extraction line into substrate and sand phases.

21 Claims, 8 Drawing Sheets

(51) Int. Cl.
   *C12M 1/107* (2006.01)
   *C12M 1/34* (2006.01)

(52) U.S. Cl.
   CPC ............ *C12M 29/00* (2013.01); *C12M 41/40* (2013.01); *Y02E 50/343* (2013.01)

(56) References Cited

U.S. PATENT DOCUMENTS

| | | |
|---|---|---|
| 9,540,605 B2 | 1/2017 | Niederbacher |
| 2004/0084366 A1 | 5/2004 | Anderson et al. |
| 2007/0075501 A1 | 4/2007 | Hughes |
| 2009/0068725 A1* | 3/2009 | Lutz .................. C12M 21/04 435/286.5 |
| 2014/0272568 A1* | 9/2014 | Frianeza-Kullberg .................. H01M 4/505 429/212 |
| 2015/0315535 A1 | 11/2015 | Kromus et al. |

FOREIGN PATENT DOCUMENTS

| | | |
|---|---|---|
| DE | 19615551 A1 | 12/1996 |
| DE | 29719294 U1 | 1/1998 |
| DE | 20011783 U1 | 11/2000 |
| DE | 202006002757 U1 | 6/2007 |
| DE | 102006010449 A1 | 9/2007 |
| GB | 2074997 A | 11/1981 |
| WO | 2009117754 A1 | 10/2009 |
| WO | 2014015949 A1 | 1/2014 |

* cited by examiner

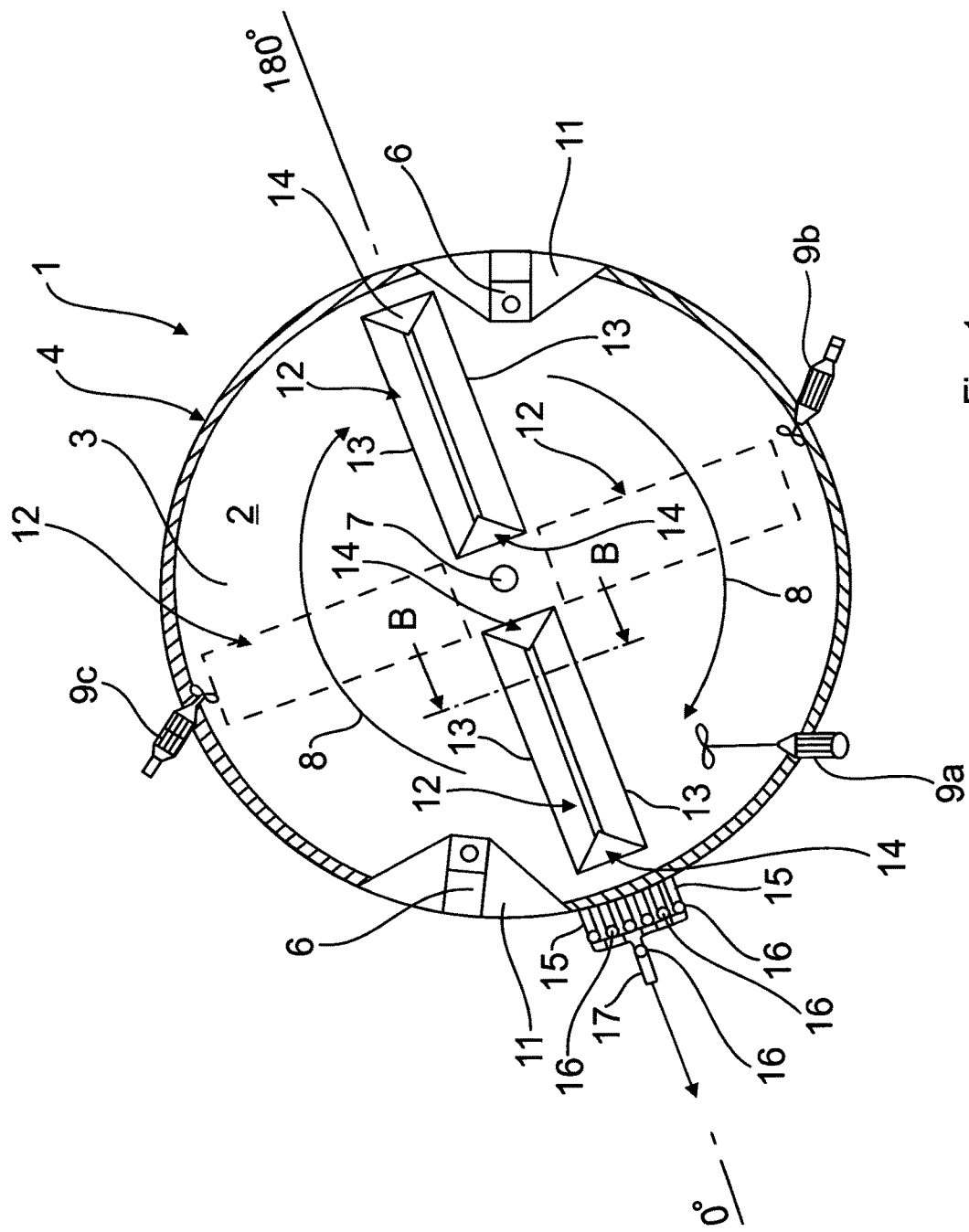

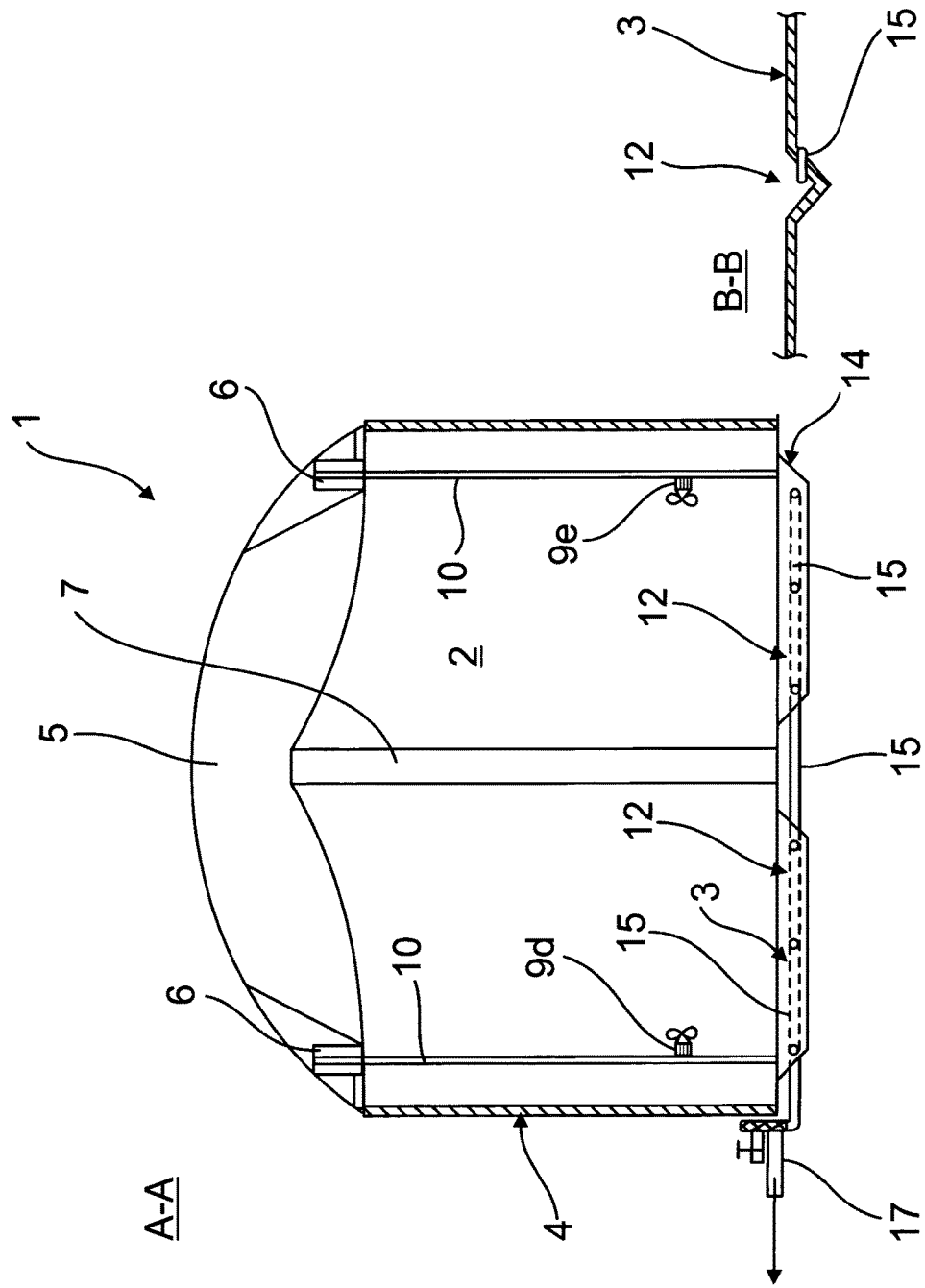

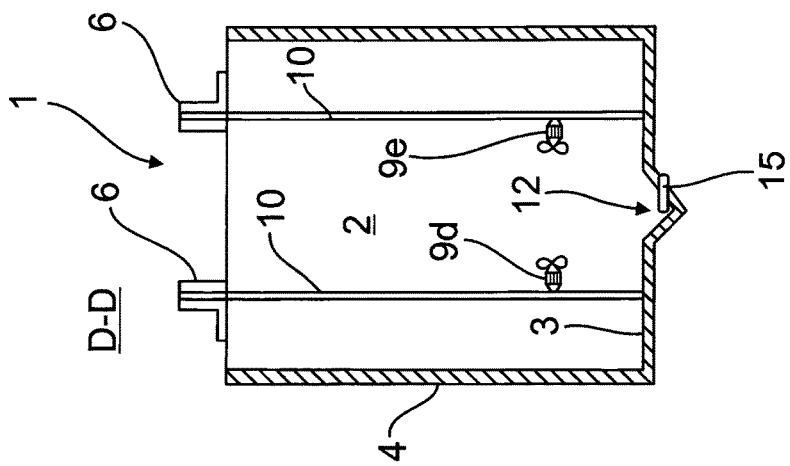
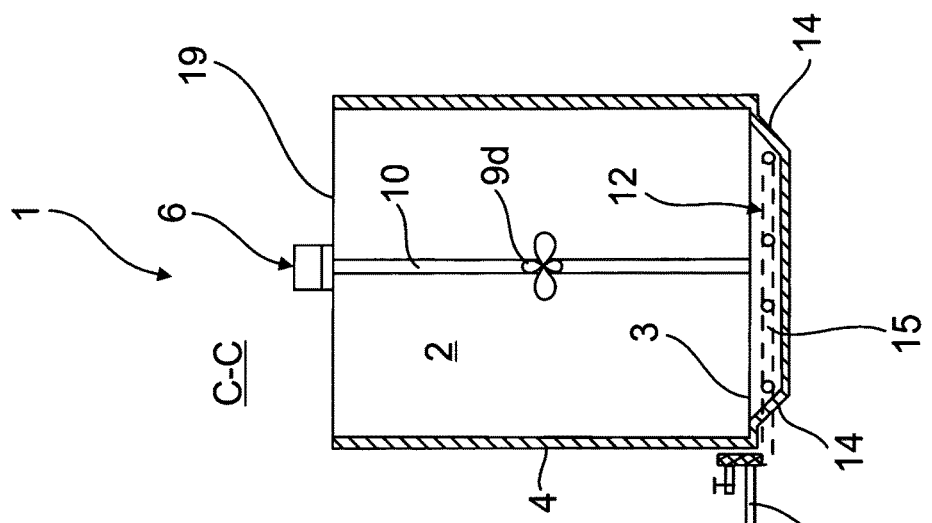
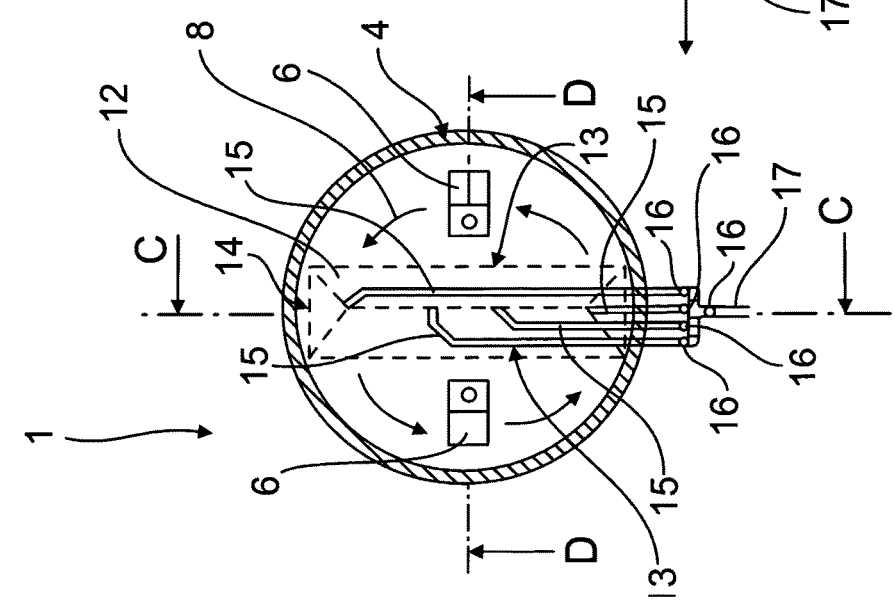

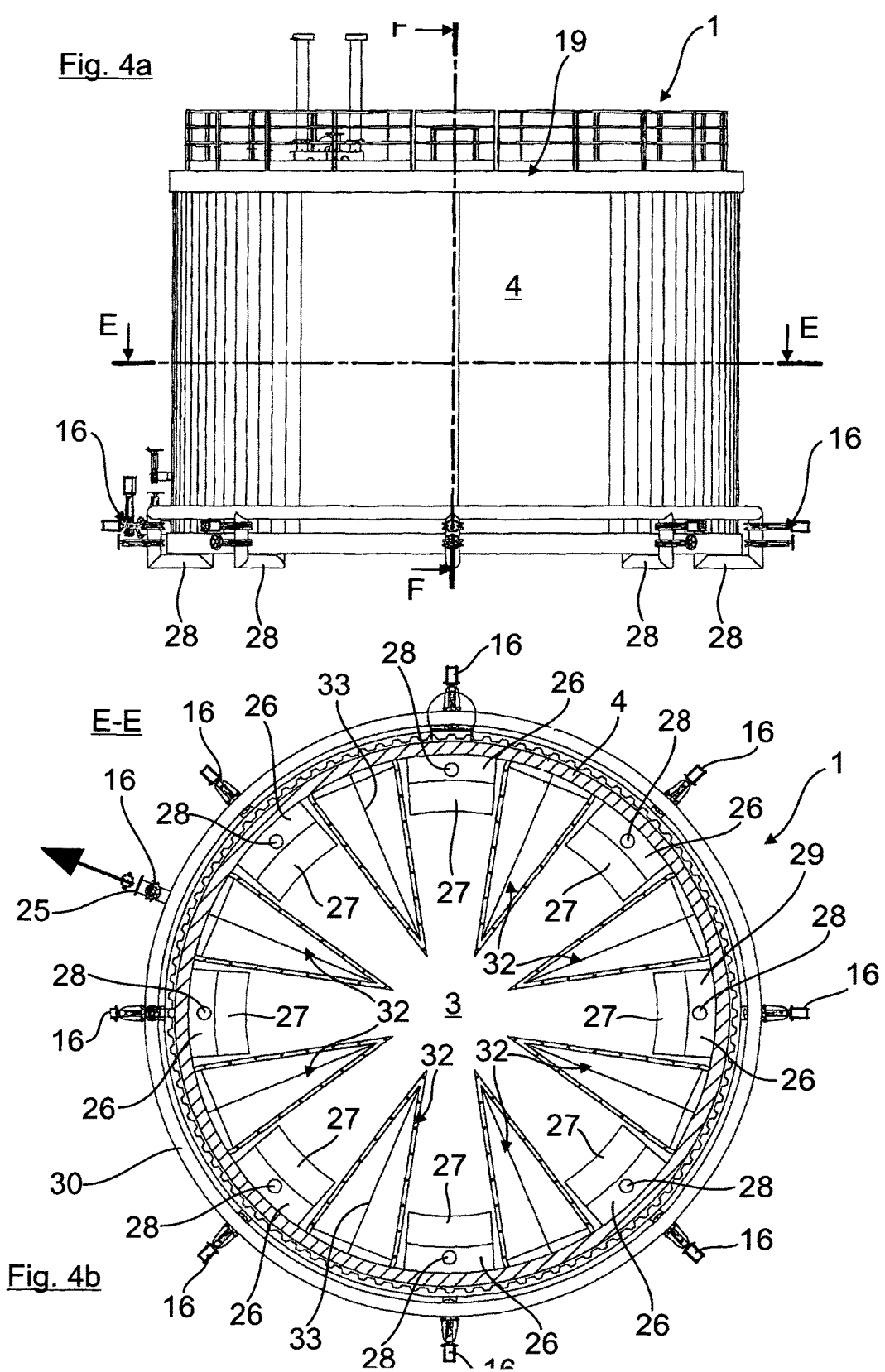

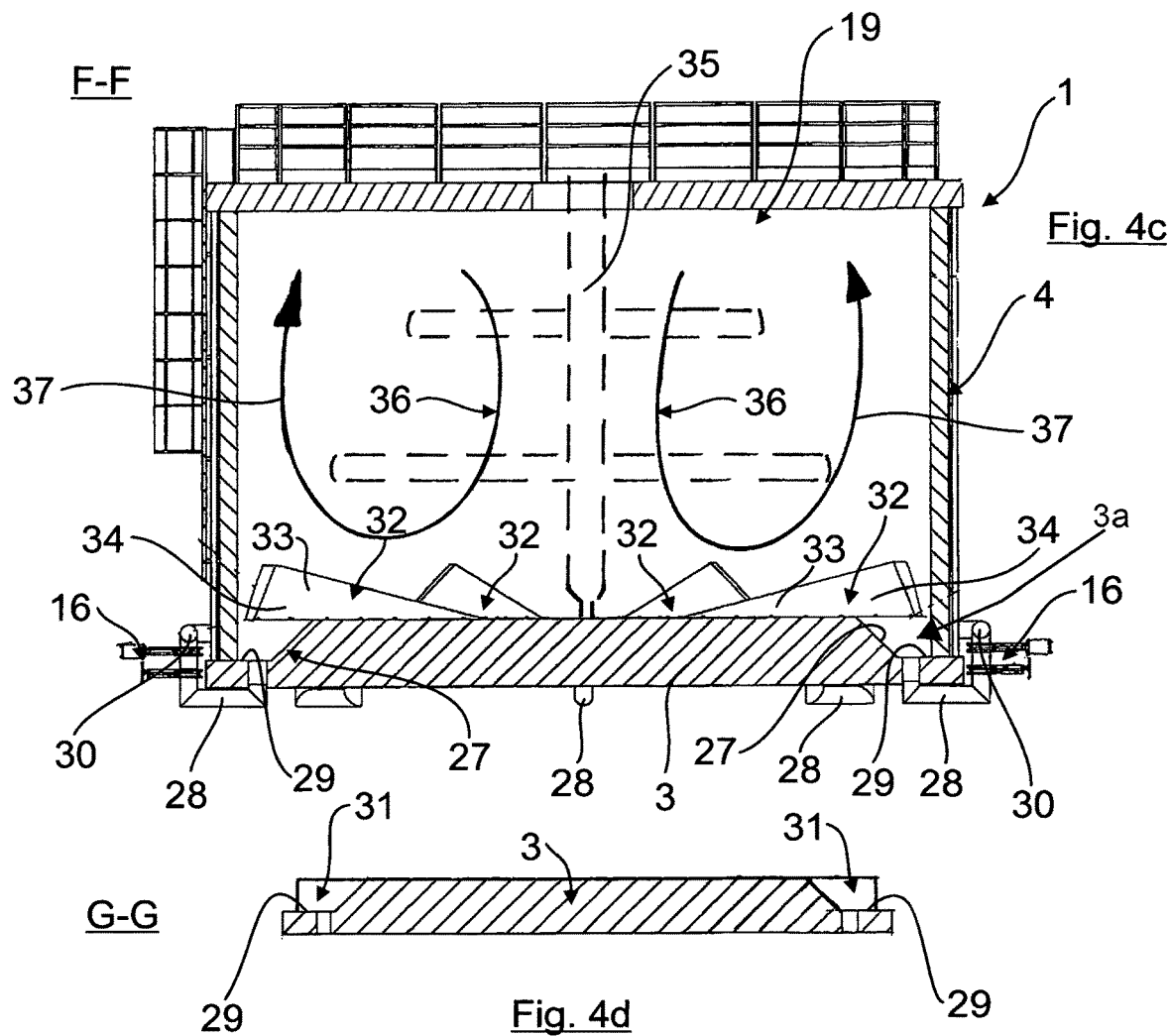
Fig. 4c
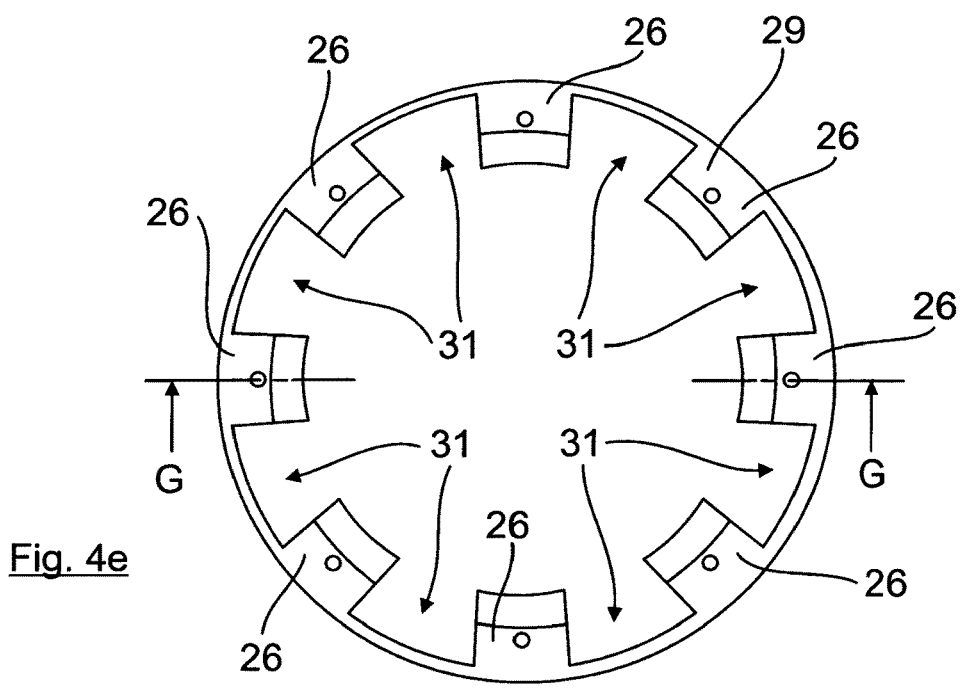
Fig. 4d
Fig. 4e

LIQUID SUBSTRATE TANK FOR A BIOGAS PLANT

BACKGROUND OF THE INVENTION

Field of the Invention

The invention relates to a liquid substrate tank for a biogas plant having a tank interior space which can be filled with a liquid substrate and having a tank base wall which delimits the tank interior space at a base and which is in particular at least regionally planar.

Liquid substrate tanks for biogas plants are generally known. These generally have a tank interior space which can be filled with a liquid substrate and which has a tank base wall which delimits the tank interior space at a base and which is in particular at least regionally planar. The tank base wall is adjoined by a tank side wall which circumferentially delimits the tank interior space and which in turn is adjoined by a cover which closes off the upwardly open tank in preferably gas-tight and liquid-tight fashion, which cover may for example be formed by a foil roof or by a horizontal covering wall, for example a concrete ceiling.

A liquid substrate tank constructed in this way may for example be a conventional fermenter tank in which the liquid substrate to be fermented is accommodated. It is likewise possible for a liquid substrate tank of said type to be a final repository tank, in which the already fermented liquid substrate is accommodated. Liquid substrate tanks of said type are generally assigned at least one agitator as a flow-generating device, by way of which the liquid substrate accommodated in the liquid substrate tank can have a targeted flow motion imparted to it for the purposes of mixing.

In particular in conjunction with liquid substrates with a high solids load, there is however the risk of said solids being deposited as a substrate-sand mixture on the base of the liquid substrate tank and accumulating there. The substrate-sand mixture which accumulates on the tank base, wherein the expression "sand" is in this case explicitly to be understood in a broad sense, considerably impairs the practical operation of a liquid substrate tank of said type in a biogas plant, such that the substrate-sand mixture that accumulates for operational reasons must be removed at regular intervals. For this purpose, it is already generally known for a liquid substrate tank of said type to be put out of operation and for the tank to be emptied in order to remove the substrate-sand mixture that has accumulated at the base. In particular in the case of relatively long operating periods, there is the risk here of the substrate-sand mixture baking onto the base wall such that the removal of the substrate-sand mixture is possible only with considerable outlay. This is evidently a cumbersome and expensive procedure, wherein furthermore, for a certain period of time, the liquid substrate tank is not available for the operation of the biogas plant.

SUMMARY OF THE INVENTION

By contrast to this, it is an object of the present invention to provide a liquid substrate tank for a biogas plant, by way of which liquid substrate tank the substrate-sand mixture that accumulates in the substrate tank for operational reasons can be removed in a simple, functionally reliable and effective manner.

Said object is achieved by way of the features of the independent patent claim described below. The subclaims relate to advantageous embodiments.

According to the independent claim, a liquid substrate tank for a biogas plant is proposed, said liquid substrate tank having a tank interior space which can be filled with a liquid substrate and having a tank base wall which delimits the tank interior space at a base and which is in particular at least regionally planar. It is provided according to the invention that, in the tank base wall, there is formed at least one trough-like depression which extends over a predefined subregion of the tank base wall, to which and/or into which depression at least one extraction line of an extraction device is led. The extraction device has a control and/or regulation device by way of which the extraction device can be actuated such that a substrate-sand mixture which collects in the at least one trough-like depression for operational reasons can be extracted from the at least one trough-like depression, and thus from the tank interior space, via the at least one extraction line. The extraction device furthermore has at least one receiving and/or sedimentation tank, in particular a separator, which is connected in terms of flow to the at least one extraction line and in which the substrate-sand mixture extracted via the at least one extraction line can be received, in particular can be separated, in conjunction with a separator, into a substrate phase and a sand phase.

The at least one trough-like depression on the base permits a targeted accumulation of the substrate-sand mixture that forms for operational reasons, because the suspended matter and solids which are contained in the liquid substrate and which sink to the base have a tendency to collect at the deepest point of the tank base wall. The targeted accumulation of the undesired substrate-sand mixture in the at least one trough-like depression furthermore permits a targeted, in particular automated, extraction of said undesired accumulations from the at least one trough-like depression by actuation of the extraction device by way of the control and/or regulating device. The actuation of the extraction device by way of the control and/or regulating device may be performed at defined times and/or for a defined time period. The extraction, via the at least one extraction line, of the substrate-sand mixture which collects in the at least one trough-like depression for operational reasons may in this case particularly advantageously be performed during the ongoing operation of a liquid substrate tank, that is to say the liquid substrate tank does not have to be put out of operation and emptied in order to extract the undesired substrate-sand mixture that accumulates there.

The receiving and/or sedimentation tank is preferably a separator in which the substrate-sand mixture extracted via the at least one extraction line can be separated into a substrate phase and into a sand phase. It is thus possible in a simple manner to ensure that the substrate extracted in conjunction with the sand phase can be recovered and can for example be delivered back from the separator back to the liquid substrate tank via at least one recirculation line. Alternatively or in addition, the substrate thus obtained may however also be delivered into any other suitable or similar liquid substrate tank. By contrast, the undesired sand phase is extracted from the separator and is for example supplied for a further use or is disposed of. At this point, it is mentioned once again that the expression "sand" is in this case expressly to be understood in a broad sense and is intended to encompass any suspended matter or solids which can be deposited in the manner of sediment and which can accumulate and collect on the base wall in a liquid substrate tank.

Both the extraction line and the suction-extraction line may basically be formed in a variety of ways, wherein the embodiment of the at least one extraction line as a suction-extraction line of a suction-extraction device, for example of a pump device with pump, is preferable. In a particularly preferred specific embodiment, the suction-extraction device is a vacuum and/or negative-pressure suction-extraction device which has a vacuum and/or negative-pressure pump and/or which has a vacuum and/or negative-pressure tank as a separator, in which the substrate-sand mixture is received with a pressure lower than atmospheric pressure. By way of a vacuum and/or negative-pressure suction-extraction device of said type, the pumpable substrate-sand mixture can be extracted by suction from the at least one trough-like depression via the at least one suction-extraction line in a simple and functionally reliable manner.

The liquid substrate tank may be assigned at least one flow-generating device, for example at least one agitator, or the liquid substrate tank may have at least one such flow-generating device. By way of said at least one flow-generating device, a liquid substrate accommodated in the liquid substrate tank can flow in a predefined substrate flow direction and/or at a predefined substrate flow speed above and/or along the tank base wall. In this way, the liquid substrate accommodated in the liquid substrate tank can have imparted to it a targeted flow of said type which promotes the deposition and accumulation of the solids as a substrate-sand mixture in the at least one trough-like depression. In a particularly preferred first specific embodiment, it may be provided here that the at least one flow-generating device is arranged in the liquid substrate tank such that, when said flow-generating device is actuated, the liquid substrate can have imparted to it a rotating flow preferably about a vertical tank axis.

The at least one trough-like depression may likewise basically be formed in a wide variety of ways, for example may run in curved or spiral-shaped fashion in the tank base wall. An embodiment is however particularly preferable in which at least one trough-like depression is formed by at least one extraction channel formed in the tank base wall, preferably by an elongate extraction channel, most preferably by an elongate extraction channel which runs substantially rectilinearly or, at least in one subregion, in curved fashion. Here, the expression "elongate" refers to any rectilinear or possibly also curved extent of an extraction channel in the case of which the longitudinal sides are longer than the transverse or narrow sides of the extraction channel. An extraction channel of said type can be formed in a tank base wall in a simple manner, and promotes a deposition of the solids as a substrate-sand mixture in the tank base wall.

The at least one extraction channel is preferably arranged in the tank base wall such that said extraction channel lies in the flow path of the liquid substrate flowing over the tank base wall. Here, it is particularly preferably provided that multiple extraction channels spaced apart from one another in a substrate flow direction are arranged in the tank interior space such that said extraction channels lie in the flow path of the liquid substrate flowing over the tank base wall. In this way, an effective deposition of the solids in the liquid substrate in the at least one extraction channel is possible. Here, an embodiment is particularly preferable in which the at least one elongate extraction channel is, with regard to its longitudinal side which is longer than the narrow side, oriented and arranged substantially perpendicular to the substrate flow direction in the tank interior space. Here, in turn, an embodiment is particularly advantageous in which not just one but multiple elongate extraction channels spaced apart from one another in a substrate flow direction are, with regard to their longitudinal side, arranged substantially perpendicular to the substrate flow direction in the tank interior space. The extraction channels may possibly also be assigned a diverting element which projects in elevated fashion from the tank base wall and which promotes the accumulation and deposition of the solids in the associated extraction channel. A diverting element of said type may for example be arranged along the longitudinal side of an elongate extraction channel, and may for example slope obliquely downward toward the extraction channel. A diverting element of said type may extend only over a subregion of the longitudinal side of the extraction channel, or else may also be arranged only in sections, or else may also extend over the entire length of an extraction channel. It is likewise possible for diverting elements of said type to be arranged to both sides of an extraction channel, and for a diverting element of said type to be arranged only on one side of the extraction channel, in this case then preferably on the second longitudinal side of the extraction channel as viewed in a flow direction.

As already stated above, there is basically a wide variety of possibilities for the arrangement of one or more extraction channels on the tank base wall. One particularly effective solution provides that a single extraction channel or at least two extraction channels situated spaced apart from one another and one behind the other in the longitudinal direction is or are provided, which extends as a diametrically running extraction channel between diametrically oppositely situated base wall regions of the liquid substrate tank. With a diametrically running extraction channel of said type, it is ensured that said extraction channel extends substantially over the entire diameter of a liquid substrate tank, and thus an altogether efficient accumulation and collection of the solids as a substrate-sand mixture in the at least one extraction channel is ensured. Such a construction is particularly advantageous in conjunction with a liquid substrate tank, in particular a liquid substrate tank which has a cylindrical inner contour, which has a vertical tank axis, preferably a vertical tank central axis, about which the liquid substrate rotates when the at least one flow-generating device is actuated, wherein the diametrically running extraction channel formed by the at least one extraction channel then in this case extends to both sides of the vertical tank axis. This has the effect that a substrate part, rotating about the vertical tank axis, of the liquid substrate passes twice over the diametrically running extraction channel during one 360° revolution about the vertical tank axis, for example at 0° and 180°, which ensures a particularly effective and reliable deposition of the solids in the at least one extraction channel.

Such a liquid substrate tank which has a diametrically running extraction channel thus permits an effective deposition of solids, which is also possible with a liquid substrate tank, in particular a liquid substrate tank which has a cylindrical inner contour, which has a vertical tank axis, in particular a vertical tank central axis, about which the liquid substrate rotates when the at least one flow-generating device is actuated, and in the case of which multiple extraction channels are provided which are spaced apart from one another in a flow direction, which extraction channels extend outward in radial or stellate fashion from the vertical tank axis. Here, the circumferential spacing of the extraction channel is preferably in each case identical, though may possibly also differ. With such a construction, too, which may in particular also constitute a supplementation of the diametrically running extraction channel, a particularly effective and targeted deposition of solids is possible. Such a construction with multiple extraction channels is suitable in particular for tanks of relatively large volume.

The at least one extraction channel itself may basically have any suitable geometry. The at least one extraction channel particularly preferably has a V-shaped or funnel-shaped cross section which promotes the extraction, or extraction by suction, of the substrate-sand mixture from the extraction channel.

For example, the at least one extraction line may be formed by at least one horizontal extraction line which runs, in relation to the tank vertical axis, in a horizontal plane at the level of the at least one extraction channel, which extraction line opens laterally, in particular in an extraction channel side wall region, into the associated extraction channel. With a lateral opening-in configuration of said type, the risk of blockage of the extraction line is considerably reduced, such that here, it is also possible to use extraction lines with a relatively small cross section. The latter is an advantage in particular if, in conjunction with the elongate extraction channels, and in accordance with a particularly preferred embodiment, multiple extraction lines spaced apart from one another in an extraction channel longitudinal direction open into the at least one extraction channel. Such multiple spaced-apart extraction lines which open into an extraction channel yield a particularly functionally reliable, automatable extraction of the substrate-sand mixture from the respective extraction channel. For example, in a specific embodiment, it may be provided that in each case one extraction line opens into the oppositely situated channel end regions as viewed in the extraction channel longitudinal direction. In particular in conjunction with relatively large elongate extraction channels, an embodiment is furthermore advantageous in which in each case one extraction line opens into the oppositely situated channel end regions as viewed in the extraction channel longitudinal direction and, furthermore, at least one extraction line opens into the channel intermediate region situated between said two channel end regions. Depending on the length of the extraction channel, it is thus also possible for multiple mutually spaced-apart extraction lines to open into the channel intermediate region situated between the two channel end regions.

To ensure an individual extraction of the substrate-sand mixture from the extraction channels, it is provided in a particularly preferred embodiment that at least the extraction lines assigned to different extraction channels, but preferably each of the extraction lines, can be opened and shut off by way of a shut-off element which is separately actuable by the regulating and/or control device.

For a targeted supply of the extracted substrate-sand mixture to the receiving and/or sedimentation tank formed in particular by a separator, it is preferably the case that all of the extraction lines open into a collecting line which can preferably be opened and closed by way of a shut-off element in a manner controlled by way of the control and/or regulating device.

Alternatively or in addition to the above-described arrangement of the extraction lines substantially on the base, it may however also be provided that the at least one extraction line or at least one of the extraction lines is formed by at least one extraction probe which is inserted in particular in gas-tight fashion through a tank wall (which may be the tank roof and/or the tank side wall and/or the tank base wall) into the tank interior space and which is led in the tank interior space as far as into the region of an associated extraction channel. Here, an embodiment is particularly preferable in which the at least one extraction line or at least one of the extraction lines is formed by at least one extraction probe which, in relation to the tank vertical axis, is inserted in gas-tight fashion from above through the tank roof, or from the side through the tank side wall, into the tank interior space and which is led in the tank interior space as far as into the region of an associated extraction channel.

For a particularly effective extraction, by suction, of the substrate-sand mixture that has accumulated in the associated extraction channel, the at least one extraction probe is preferably mounted so as to be adjustable in height, in particular in such a way that, when said tank has been filled with liquid substrate, a skirt arranged on the tank roof dips into said liquid substrate, and the extraction probe is led in gas-tight and height-adjustable fashion through the skirt into the tank interior space.

In this case, too, an embodiment is advantageous in which the extraction probes assigned to the different extraction channels, preferably even each of the extraction probes, can be opened and shut off by way of a shut-off element which is separately actuable by the regulating and/or control device.

According to a further alternative embodiment, the liquid substrate tank is assigned at least one flow-generating device, in particular at least one agitator, or the liquid substrate tank has at least one such flow-generating device. When the at least one flow-generating device is actuated, a liquid substrate received in the liquid substrate tank flows in a predefined substrate flow direction and/or at a predefined substrate flow speed above and/or along the tank base wall. Here, it is preferably provided that the at least one flow-generating device is arranged in the liquid substrate tank such that, when said flow-generating device is actuated, the liquid substrate can have imparted to it a cylindrical flow with at least one flow cylinder which moves, in relation to the tank vertical axis, from top to bottom, preferably about a horizontal tank axis, in particular with an upward flow at the side of the tank side wall. Such a substrate flow is advantageous in particular if, according to a particularly preferred embodiment, it is provided that the tank base wall has, in the transition region to the tank side wall, multiple mutually spaced-apart trough-like depressions at an edge. Here, said trough-like depressions are preferably formed so as to be uniformly spaced apart from one another and/or in each case of identical form.

For a particularly effective accumulation and collection of the solids as a substrate-sand mixture in the trough-like depressions, it is preferably provided that the trough-like depressions lie in each case in the flow path of a flow cylinder of the liquid substrate. Here, an embodiment is particularly preferable in which the trough-like depressions lie in each case in the flow path of a flow cylinder with an upward flow at the side of the tank wall, because in this way, it can be ensured even more effectively that the suspended matter or solids striking the tank wall fall in the direction of the tank base wall and thus in the direction of the trough-like depression.

The trough-like depressions are preferably formed by recesses at an edge in the base wall, which depressions have, inwardly in the direction of the tank center, a ramp-shaped bevel, which in turn transitions into a preferably planar base wall region which is adjacent in the direction of the tank center, and/or which depressions are delimited in the direction of the tank outer side by a tank side wall region. The ramp-shaped bevel promotes the accumulation of the solids in the respective trough-like depression. By contrast, the tank side wall region simultaneously serves, in a dual function, as a wall which delimits the respective trough-like depression.

It is preferably the case that in each case at least one, preferably a single, extraction line opens into a trough-like depression, specifically preferably into a preferably planar trough base region of the respective trough-like depression. With such an arrangement of an extraction line, a functionally reliable extraction of the substrate-sand mixture that accumulates in the respective trough-like depression is possible.

For an individual extraction of the solids that accumulate as a substrate-sand mixture in the respective trough-like depressions, it is preferably provided that at least the extraction lines assigned to different trough-like depressions, preferably each of the extraction lines, can be opened and shut off by way of a shut-off element which is separately actuable by the regulating and/or control device.

Furthermore, according to a particularly preferred specific embodiment, it is advantageous if at least a part of the extraction lines, preferably all of the extraction lines, open out in a collecting line which preferably runs as a ring-shaped line in ring-shaped fashion around the substrate tank, which collecting line is led to the separator, and which collecting line can be closed and opened by way of a shut-off element in a manner controlled by way of the control and/or regulating device. In this way, a compact and functionally reliable supply of the extracted substrate-sand mixture to the receiving and/or sedimentation tank, which is preferably formed by a separator, is possible.

The sinking of the solids, and thus the accumulation thereof as a substrate-sand mixture in the respective trough-like depressions, can furthermore additionally be promoted by virtue of the base wall region having at least one elevated diverting element in a diverting base wall region situated between the trough-like depressions. Here, the at least one diverting element may narrow inwardly in the direction of the tank center proceeding from the edge region at the base wall side. It is furthermore preferably provided that the diverting element is of roof-shaped form, in particular of saddle-roof-shaped or gable-roof-shaped form, with a crown edge, and has side surfaces which slope downward toward the adjacent trough-like depressions. Such a construction considerably promotes the sinking and deposition of the solids particles.

Here, an embodiment is particularly preferable in which the diverting elements, which are preferably of identical form, extend inwardly in the direction of the tank center beyond the trough-like depressions, which are formed only in the base wall region at the edge. Here, an embodiment is preferable in which the liquid substrate tank, which has a cylindrical inner contour, has a vertical tank central axis toward which the inner ends of the diverting elements are oriented.

It is self-evident that the diverting elements may basically be formed in a wide variety of ways, for example by way of separate components, such as for example sheet-metal components, which are fixedly connected, for example fixedly screwed, to the tank base wall.

In conjunction with the above-described embodiment with trough-like depressions arranged at the edge, it is the case in particular that a construction is advantageous in which the flow-generating device is formed by a central agitator arranged centrally in the liquid substrate tank, which central agitator extends in the tank vertical axis direction.

BRIEF DESCRIPTION OF THE SEVERAL VIEWS OF THE DRAWING

Exemplary embodiments of a liquid substrate tank according to the invention for a biogas plant will be discussed in more detail below on the basis of a drawing.

In the drawing:

FIG. 1a schematically shows a plan view of a liquid substrate tank of a biogas plant according to a first embodiment, with two extraction channels extending diametrically over a tank base wall.

DESCRIPTION OF THE INVENTION

Figure 1B:
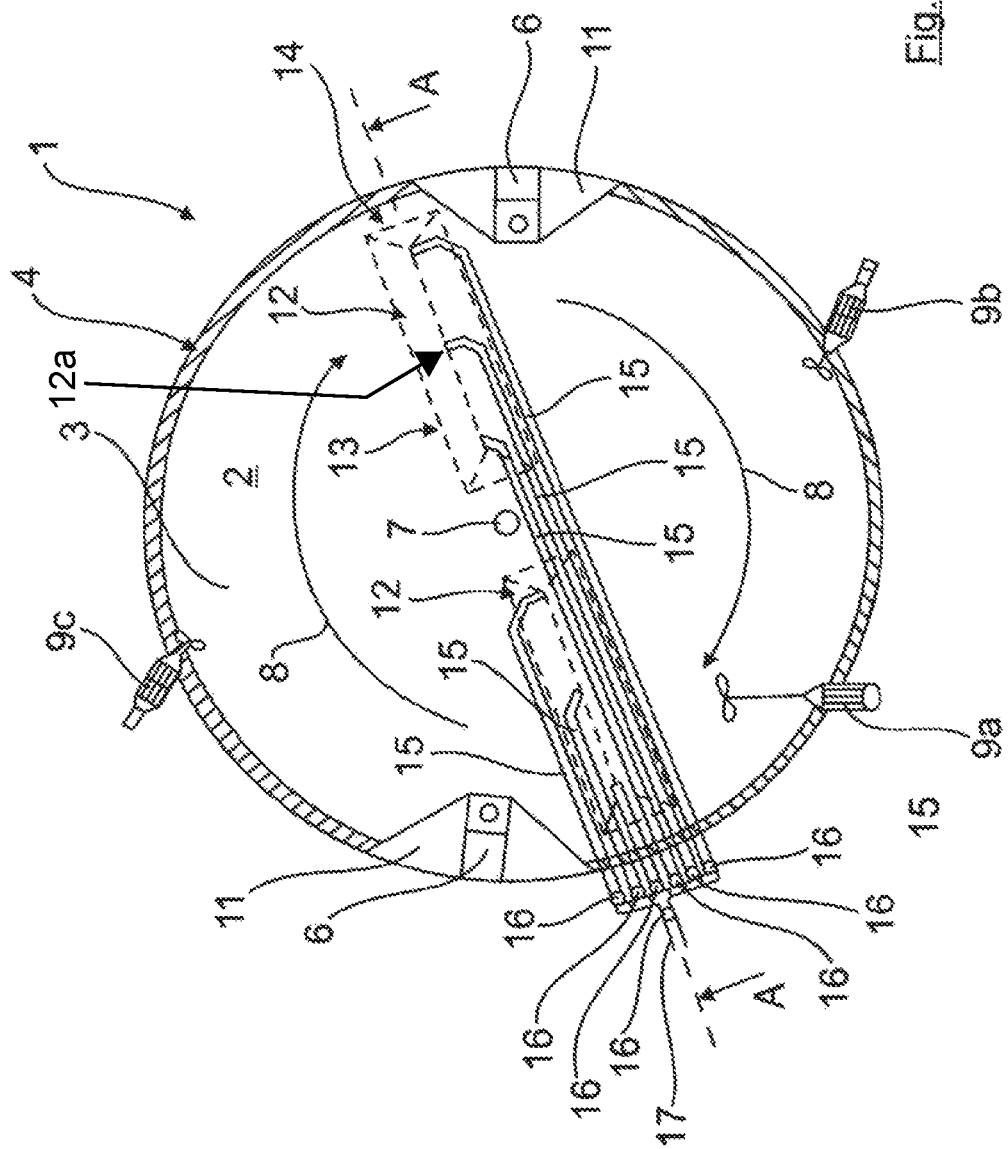
FIG. 1b shows the construction as per FIG. 1a with extraction lines leading to the extraction channels, FIG. 1c schematically shows a sectional view along the line A-A in FIG. 1b, FIG. 1d schematically shows a sectional view along the line B-B in FIG. 1a, FIG. 2a schematically shows a plan view of a second embodiment of a liquid substrate tank according to the invention, with a single diametrically running extraction channel, FIG. 2b schematically shows a sectional view along the line C-C in FIG. 2a, FIG. 2c schematically shows a sectional view along the line D-D in FIG. 2a, FIG. 2d schematically shows an illustration corresponding to FIG. 2a with an extraction channel illustrated in detail.

FIG. 1a shows, schematically and by way of example, a plan view of a first embodiment of a liquid substrate tank 1 according to the invention for a biogas plant, which liquid substrate tank has a tank interior space 2 which can be filled with liquid substrate, a tank base wall 3 which delimits the tank interior space 2 at a base side and which in this case is of planar form, and, as can be seen in particular from FIG. 1c, a tank side wall 4 which circumferentially delimits the tank interior space 2. The tank interior space 2 is in this case covered by way of example, as per FIG. 1c, by a foil roof 5 such as is known per se.

To generate a flow of the liquid substrate (not shown in detail here) which rotates about the vertical tank central axis 7 (corresponding to the arrows 8), multiple agitators 9a to 9e are provided so as to be circumferentially spaced apart from one another, which agitators are shown here merely by way of example and schematically. Whereas the agitators 9a, 9b and 9c are in this case merely by way of example and schematically arranged spaced apart from one another on the circular cylindrical tank side wall 4, the agitators 9d and 9e (see FIG. 1c) are held in height-adjustable and/or pivotable fashion on a vertical guide mast 10, wherein the guide mast 10 is mounted or held by way of its upper end in a service shaft 6, via which it is possible for installation and servicing equipment to access the agitators 9d and 9e, and via which the agitators 9d, 9e can be lifted out of the container interior space 2. The service shafts 6 themselves are supported and held, for example in conjunction with a pedestal plate 11, on the tank side wall 4, as can be seen in particular from FIG. 1a.

As can also be seen when viewing FIGS. 1a to 1d together, it is the case here, by way of example, that two elongate and substantially rectilinearly running extraction channels are formed in the tank base wall 3, which extraction channels extend in each case outwardly proceeding from the tank central axis 7 to the tank side wall 4 and thus form a substantially diametrically running extraction channel between diametrically oppositely situated tank base wall regions or tank side wall regions of the liquid substrate tank 1.

As can also be seen in particular from FIG. 1a, the extraction channels are in this case, with regard to their longitudinal side, oriented and arranged substantially perpendicular to the rotating substrate flow direction in the tank interior space 2, such that a substrate part, rotating about the vertical tank central axis 7, of the liquid substrate passes twice over the two extraction channels 12, which form one diametrically running extraction channel, during one 360° revolution about the vertical tank central axis 7, specifically, in relation to the extraction channels 12, at 0° and 180°.

As is illustrated merely schematically and by way of dashed lines in FIG. 1a, it would however also be possible for multiple extraction channels 12 to be provided and formed in the tank base wall 3, which extraction channels then altogether extend outward in radial or stellate fashion from the vertical tank central axis 7.

As can be seen from FIG. 1d, which shows a section along the line B-B in FIG. 1a, the extraction channels have a preferred V-shaped or funnel-shaped cross section, such that the inner walls of the longitudinal sides 13 of the extraction channel 12 slope obliquely downward toward the base center. It is likewise possible, as can be seen in particular from FIG. 1a, for the oppositely situated transverse sides 14 to have obliquely inwardly downward-sloping inner walls.

As can be seen in particular when viewing FIGS. 1b and 1c together, it is the case here that multiple extraction lines 15 spaced apart from one another in an extraction channel longitudinal direction open into each of the extraction channels 12, which extraction lines run in a horizontal plane relative to the tank vertical axis and, in this case, open in each case into the obliquely inwardly downward-sloping extraction channel side wall regions. As can be seen in particular from FIG. 1b, in each case one extraction line 15 opens into the oppositely situated channel end regions as viewed in the extraction channel longitudinal direction, whereas one extraction line 15 opens into the channel intermediate region 12a situated between said channel end regions.

Figure 5:
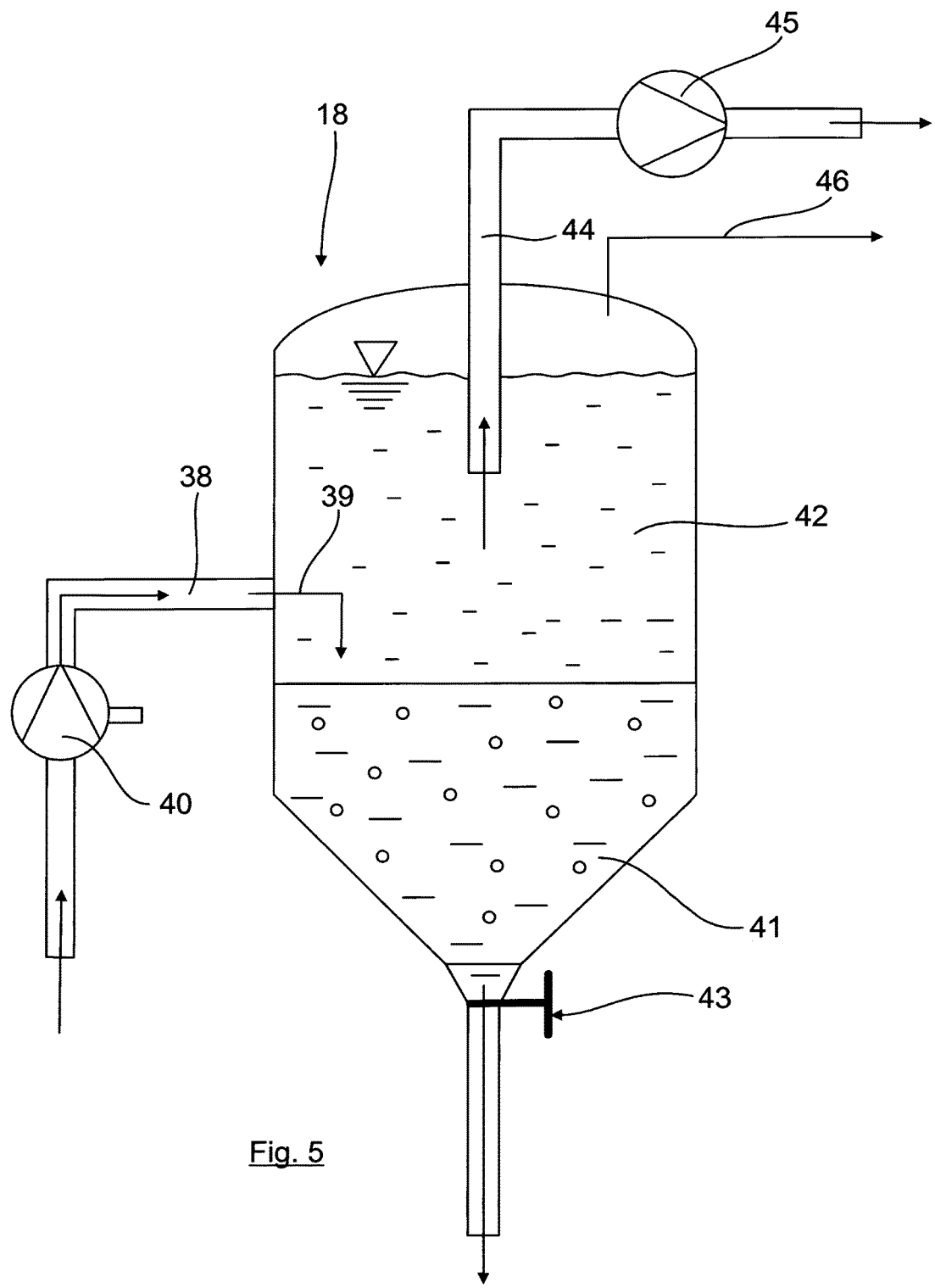

As can also be seen from FIG. 1b, it is the case here by way of example that each of the extraction lines 15 can be opened or shut off by way of a shut-off element 16 which is separately actuable by the regulating and/or control device 47, which shut-off element may for example be a slide or a valve, wherein it is furthermore provided here that all of the extraction lines 16 open into a collecting line 17, which collecting line in this case can likewise be closed and opened by way of a shut-off element 16 in a manner controlled by way of the control and/or regulating device, and which collecting line is led to a separator 18 shown in FIG. 5.

With a liquid substrate tank 1 constructed in this way, the liquid substrate can have imparted to it the rotating flow (arrow 8) schematically shown in FIGS. 1a and 1b, whereby the individual substrate subregions pass over the individual extraction channels 12 multiple times during the course of several revolutions. The solids situated in the liquid substrate in this case sink down to the tank base wall 3 and can then, owing to the rotating flow and the extraction channels 12, be deposited as a substrate-sand mixture in the extraction channels 12, from where they can be extracted via the extraction lines 15 in a manner controlled by way of the control and/or regulating device, and supplied via the collecting line 17 to the separator 18. The shut-off elements 16 can in this case be individually actuated by way of the control and/or regulating device, and thus individual extraction, by suction, of the substrate-sand mixture from the extraction channels 12 can be realized.

FIGS. 2a to 2d show an embodiment alternative to that in FIGS. 1a to 1d, wherein the liquid substrate tank 1 has for example a smaller diameter than that of the embodiment as per FIG. 1d. Furthermore, in this case, only a single extraction channel 12 extends diametrically between oppositely situated edge regions of the tank base wall 3 or between oppositely situated side wall regions of the tank side wall 4.

In this case, too, extraction lines 15 which run horizontally into the extraction channel 12 in relation to the tank vertical axis direction open, spaced apart from one another, into the elongate extraction channel 12, specifically, in principle, analogously to the embodiment of FIGS. 1a to 1d, wherein, again merely by way of example, two further mutually spaced-apart extraction lines 15 open into the channel intermediate region between the two extraction lines 15 which open into the oppositely situated channel end regions.

As a further difference in relation to the embodiment as per 1a to 1d, the tank interior space 2 in this case does not have a dome-like foil roof, but rather a planar roof-side cover 19, on which in this case, merely highly schematically and by way of example, two service shafts 6 with associated guide masts 10 and agitators 9d and 9e are arranged.

Otherwise, the construction is identical to that of FIGS. 1a to 1d, such that, with regard to the operational extraction, by suction, of the substrate-sand mixture that accumulates in the extraction channel 12 in conjunction with a rotating flow of the liquid substrate, reference is made to the statements above.

Figure 3B:
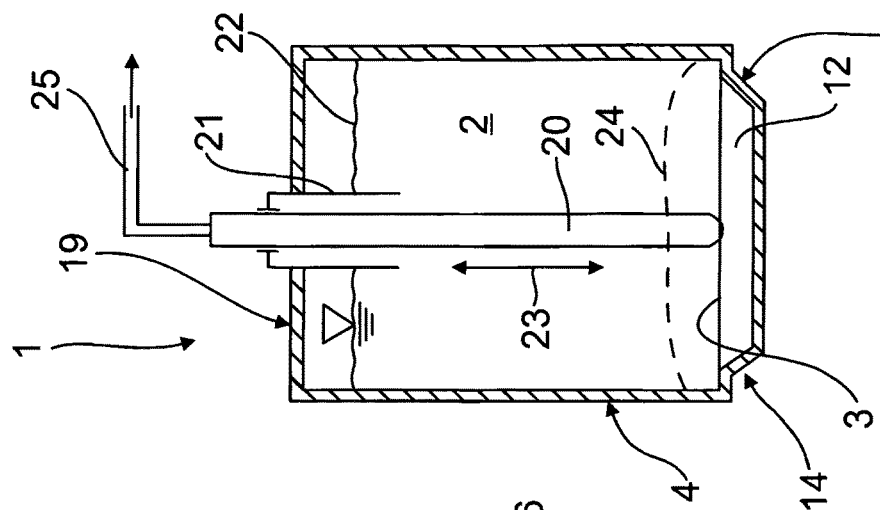
FIG. 3a shows a schematic plan view of a third embodiment of a liquid substrate tank according to the invention, with an extraction probe opening into the substrate tank from above, FIG. 3b schematically shows a cross-sectional view of the construction as per FIG. 3a, FIG. 4a schematically shows a side view of a substrate tank according to a fourth embodiment, FIG. 4b schematically shows a sectional view along the line E-E in FIG. 4a, FIG. 4c schematically shows a sectional view along the line F-F in FIG. 4a, FIG. 4d schematically shows a sectional view along the line G-G in FIG. 4e, FIG. 4e schematically shows a plan view of the tank base wall illustrated in FIG. 4d with trough-like depressions at the edge, and FIG. 5 schematically shows an exemplary embodiment of a separator in the form of a receiving and/or sedimentation tank.
Figure 3A:
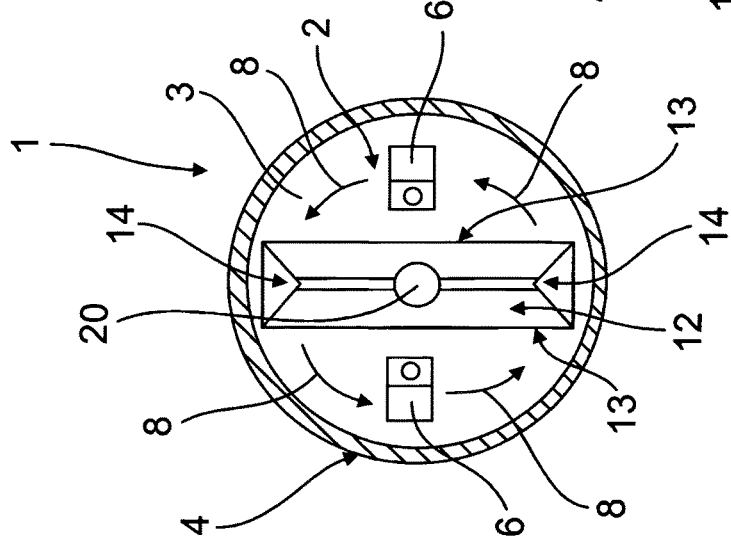
Figure 2D:
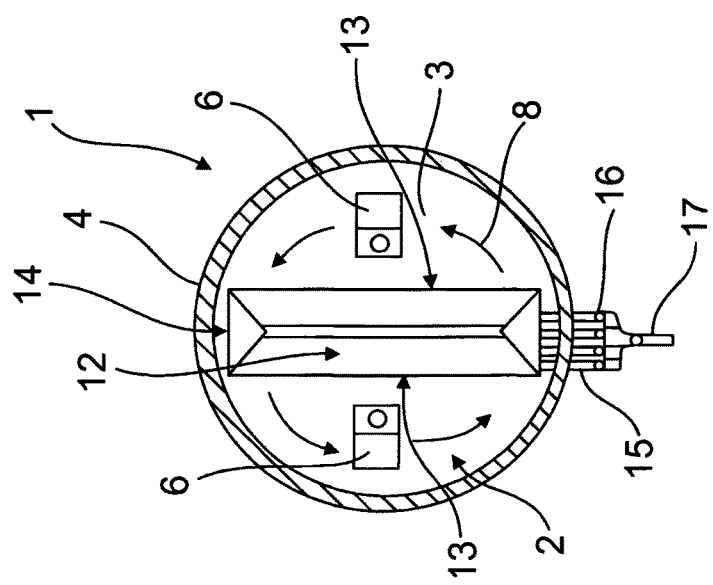

FIGS. 3a and 3b show a further alternative embodiment of a liquid substrate tank 1 according to the invention, which is designed substantially analogously to the embodiment as per FIGS. 2a to 2d, but with the difference that, here, instead of the horizontally running extraction lines on the base, an extraction probe 20 is provided as extraction line, which extraction probe, in relation to the tank vertical axis, is in this case merely by way of example introduced into the tank interior space 2 from above through the tank roof or the roof wall 19, and is led in the tank interior space 2 as far as into the region of the, by way of example, single extraction channel 12 in this case. The, by way of example, only one single extraction probe 20 in this case is furthermore preferably mounted so as to be adjustable in height, specifically preferably such that, when said tank has been filled with liquid substrate 22, a skirt 21 arranged on the tank roof dips into said liquid substrate, and the extraction probe 20 is led in gas-tight and height-adjustable fashion through the skirt 21 into the tank interior space. It is thus possible for the extraction probe 20 to be mounted and adjusted in the vertical axis direction correspondingly to the arrow 23 in FIG. 3b, which is advantageous in particular if a relatively large amount of substrate-sand mixture 24, which is to be extracted by suction, accumulates in an in particular relatively small-volume liquid substrate tank 1, especially also in the region above the extraction channel 12, as is illustrated merely highly schematically in FIG. 3b.

In this case, too, it is again possible for the extraction probe to be actuated by way of the regulating and/or control device in order to control the extraction, by suction, of the substrate-sand mixture from the extraction channel 12. Then, a corresponding recirculation line 25 leads from the extraction probe 20 to the separator 18, as illustrated by way of example in FIG. 5.

Finally, FIGS. 4a to 4d show a further alternative, fourth embodiment of a liquid substrate tank 1 according to the invention, in the case of which the tank base wall 3 has, in the transition region 3a to the tank side wall 4, multiple mutually spaced-apart, trough-like depressions 26 at the edge, which depressions are in this case for example and preferably uniformly spaced apart from one another and of substantially identical form.

The trough-like depressions 26 are in this case formed in each case by recesses at the edge in the base wall, which recesses have, inwardly toward the tank center, a ramp-shaped bevel 27, which in turn transitions into a base wall region which is adjacent in the direction of the tank center and which is in this case, by way of example, planar. Furthermore, the trough-like depressions 26 are delimited toward the tank outer side by a tank side wall region.

The trough-like depressions 26 are assigned in each case a single extraction line 28, which opens out in a planar trough base region 29 of the respective trough-like depression 26.

In this case, too, the individual extraction lines 28 can be opened and shut off in each case by way of a shut-off element which is separately actuable by the regulating and/or control device.

Furthermore, in this case, all of the extraction lines 28 open into a collecting line 30 which runs as a ring-shaped line in ring-shaped fashion around the liquid substrate tank 1 and which is led to the separator 18 and which can be closed and opened by way of a shut-off element in a manner controlled by way of the control and/or regulating device.

Furthermore, here, the tank base wall 3 has an elevated diverting element 32 in a diverting base wall region 31 which is situated between the trough-like depressions 26, which diverting element narrows inwardly in the direction of the center proceeding from the edge region at the base wall and, here, is furthermore of saddle-roof-shaped or gable-roof-shaped form with a crown edge 33, and has side surfaces 34 which slope downward in each case toward the adjacent trough-like depressions 26.

As can also be seen from FIGS. 4a to 4d, the diverting elements 32, which in this case are preferably of identical form, extend inwardly in the direction of the tank center in each case beyond the trough-like depressions 26, which are formed only in the base wall region at the edge, wherein the liquid substrate tank 1, which has a cylindrical inner contour, and which in this case merely by way of example has a horizontal tank roof 19, has a vertical tank central axis which is formed by a central agitator 35 and toward which the inner ends of the diverting elements 32 are oriented.

The diverting elements 32 may for example be produced from sheet metal, and may for example, as separate components, be fixedly connected to the tank base wall, in particular by way of screw connection.

The central agitator 35 is preferably designed such that, when said central agitator is actuated, the liquid substrate can have imparted to it a cylindrical flow with at least one flow cylinder 36 which moves, in relation to the tank vertical axis, from top to bottom about a horizontal tank axis (see FIG. 4c), with an upward flow 37 at the side of the tank side wall.

With such a construction, it is ensured that the solids contained in the liquid substrate preferentially collect at the edge and then sink downward, wherein the diverting elements 32 advantageously have the effect that the sediments are diverted or conducted in the direction of the trough-like depressions 26, from where they can then be extracted as a substrate-sand mixture via the extraction lines 28 and supplied to the separator 18.

Finally, FIG. 5 shows an exemplary schematic sketch of a separator 18, to which, via the supply line 38, which may for example be connected in terms of flow to the collecting line 17, to the recirculation line 25 or to the collecting line 30 of the different embodiments described above, in order to conduct the substrate-sand mixture, which is extracted from the liquid substrate tank 1 via the respective extraction lines 15 or the extraction probe 20, which likewise forms an extraction line, into the interior space of the separator 18 (arrow 39). Here, the extraction lines are in each case a constituent part of a suction-extraction device which is preferably in the form of a vacuum and/or negative-pressure suction-extraction device, which has a vacuum and/or negative-pressure pump 40 by way of which the pumpable substrate can be extracted, by suction, from the respective extraction channel 12 or from the respective trough-like depression 26 via the respectively opened extraction lines.

The separator 18 may itself furthermore be in the form of a vacuum and/or negative-pressure tank, in which the substrate-sand mixture is received with a pressure lower than atmospheric pressure. In the separator 18, the substrate-sand mixture is separated into a sand phase 41 and a substrate phase 42, wherein the sand phase 41 then accumulates at the base in the separator 18, and there, can be extracted for example in targeted fashion in a manner controlled by opening of a shut-off element 43, which is actuated by the control and/or regulating device. It is likewise possible for the substrate phase 42 to be recirculated as a liquid phase via a recirculation line 44 into the liquid substrate tank 1, which may be realized for example by way of a pump 45 as delivery device. If post-fermentation occurs in the separator 18 and gas forms, said gas can likewise be extracted by way of an extraction line 46 and supplied for a further use.

LIST OF REFERENCE DESIGNATIONS

1 Liquid substrate tank
2 Tank interior space
3 Tank base wall
4 Tank side wall
5 Foil roof
6 Service shafts
7 Tank central axis
8 Arrows
9a to 9e Agitators
10 Guide mast
11 Pedestal plate
12 Extraction channel 13 Longitudinal sides
14 Transverse sides
15 Extraction lines
16 Shut-off element
17 Collecting line
18 Separator
19 Roof wall
20 Extraction probe
21 Skirt
22 Liquid substrate
23 Arrow
24 Substrate-sand mixture
25 Recirculation line
26 Trough-like depressions
27 Bevel
28 Extraction line
29 Planar trough base region
30 Collecting line
31 Diverting base wall region
32 Diverting element
33 Crown edge
34 Downward-sloping side surfaces
35 Central agitator
36 Flow cylinder
37 Upward flow
38 Supply line
39 Arrow
40 Vacuum and/or negative-pressure pump
41 Sand phase
42 Substrate phase
43 Shut-off element
44 Recirculation line
45 Pump
46 Gas extraction

The invention claimed is:

1. A liquid substrate tank for a biogas plant, the liquid substrate tank comprising:
    a tank base wall disposed at a tank base for delimiting an tank interior space to be filled with a liquid substrate;
    at least one trough-shaped depression formed in a predefined subregion of and extending over said tank base wall;
    a cylindrical inner tank contour;
    an extraction device having at least one extraction line being guided to or into said at least one trough-shaped depression;
    said extraction device having a control or regulation device configured to actuate said extraction device for extracting a substrate-sand mixture collecting in said at least one trough-shaped depression during operation from said at least one trough-shaped depression and from said tank interior space through said at least one extraction line;
    said extraction device having at least one receiving or sedimentation tank being connected to said at least one extraction line for receiving a flow of the substrate-sand mixture extracted through said at least one extraction line;
    said at least one trough-shaped depression forming at least one elongate extraction channel formed in said tank base wall, said at least one elongate extraction channel formed in said tank base wall lying in a flow path of the liquid substrate flowing over said tank base wall, and said at least one elongate extraction channel having a longitudinal side oriented and disposed perpendicular to a substrate flow direction in said tank interior space; and
    at least one flow-generating device or agitator being actuable for causing a liquid substrate accommodated in the liquid substrate tank to flow in at least one of a predefined substrate flow direction or at a predefined substrate flow speed at least one of above or along said tank base wall;
    said at least one flow-generating device or agitator being disposed in the liquid substrate tank and configured to impart a rotating flow or a rotating flow about a vertical tank axis to the liquid substrate upon said at least one flow-generating device or agitator being actuated.

2. The liquid substrate tank according to claim 1, wherein said tank base wall is at least regionally planar, and said at least one receiving or sedimentation tank is a separator for separating the substrate-sand mixture into a substrate phase and a sand phase.

3. The liquid substrate tank according to claim 2, which further comprises:
    a collecting line leading from said at least one extraction line to said receiving or sedimentation tank or separator; and
    a shut-off element being controlled by said control or regulating device for opening and closing said collecting line.

4. The liquid substrate tank according to claim 1, wherein said extraction device is a suction-extraction device, and said at least one extraction line is a suction-extraction line of said suction-extraction device.

5. The liquid substrate tank according to claim 4, wherein said suction-extraction device is a vacuum or negative-pressure suction-extraction device having at least one of:
    a vacuum or negative-pressure pump for extracting the pumpable substrate-sand mixture by suction from said at least one trough-shaped depression through said at least one suction-extraction line, or
    a vacuum or negative-pressure tank acting as separator, in which the substrate-sand mixture is received with a pressure lower than atmospheric pressure.

6. The liquid substrate tank according to claim 1, wherein said at least one extraction channel includes multiple extraction channels being spaced apart from one another in a substrate flow direction, being disposed in said tank interior space and lying in a flow path of the liquid substrate flowing over said tank base wall.

7. The liquid substrate tank according to claim 1, wherein said at least one extraction channel includes multiple elongate extraction channels being spaced apart from one another in a substrate flow direction and each having a longitudinal side disposed perpendicular to a substrate flow direction in said tank interior space.

8. The liquid substrate tank according to claim 1, wherein said at least one extraction channel is a single extraction channel or at least two extraction channels being spaced apart from one another and one behind the other in a longitudinal direction and extending as a diametrically running extraction channel between diametrically oppositely disposed base wall regions of the liquid substrate tank.

9. The liquid substrate tank according to claim 8, wherein the liquid substrate tank has a vertical tank central axis about which the liquid substrate rotates when said at least one flow-generating device or agitator is actuated, and said diametrically running extraction channel extends to two sides of said vertical tank axis.

10. The liquid substrate tank according to claim 9, wherein said at least one flow-generating device or agitator causes a substrate part of the liquid substrate rotating about said vertical tank axis to pass twice over said diametrically running extraction channel during one 360° revolution about said vertical tank axis.

11. The liquid substrate tank according to claim 1, wherein:
the liquid substrate tank has a cylindrical inner contour and a vertical tank central axis about which the liquid substrate rotates when said at least one flow-generating device or agitator is actuated; and
said at least one extraction channel includes multiple extraction channels being spaced apart from one another in a flow direction and extending outward in radial or stellate fashion from said vertical tank axis.

12. The liquid substrate tank according to claim 1, wherein said at least one extraction channel has a V-shaped or funnel-shaped cross section.

13. The liquid substrate tank according to claim 1, wherein said at least one extraction line is at least one horizontal extraction line running, relative to a tank vertical axis, in a horizontal plane at a level of said at least one extraction channel, and said at least one horizontal extraction line opens laterally or in an extraction channel side wall region into said at least one extraction channel.

14. The liquid substrate tank according to claim 1, wherein said at least one extraction line includes multiple extraction lines being spaced apart from one another in an extraction channel longitudinal direction and opening into said at least one extraction channel, and each of said extraction lines opens into an oppositely situated channel end region in an extraction channel longitudinal direction.

15. The liquid substrate tank according to claim 1, wherein said at least one extraction line includes multiple extraction lines being spaced apart from one another in an extraction channel longitudinal direction and opening into said at least one extraction channel, each of said extraction lines opens into an oppositely situated channel end region in an extraction channel longitudinal direction, and at least one extraction line opens into a channel intermediate region disposed between two channel end regions.

16. The liquid substrate tank according to claim 1, wherein:
said at least one extraction line includes at least some extraction lines associated with different extraction channels; and
a shut-off element is separately actuable by said regulating or control device for opening and shutting off at least said extraction lines associated with different extraction channels or for opening and shutting off each of said extraction lines.

17. The liquid substrate tank according to claim 1, which further comprises a tank wall, said at least one extraction line being formed by at least one extraction probe being inserted in a gas-tight manner through said tank wall into said tank interior space and being led in said tank interior space as far as into a vicinity of said at least one extraction channel.

18. The liquid substrate tank according to claim 1, which further comprises a tank roof and a tank side wall, said at least one extraction line being formed by at least one extraction probe and being inserted, relative to a tank vertical axis, in a gas-tight manner from above through said tank roof or from a side through said tank side wall, into said tank interior space and being led in said tank interior space as far as into a vicinity of said at least one extraction channel.

19. The liquid substrate tank according to claim 18, which further comprises a skirt disposed on said tank roof and dipping into the liquid substrate when the liquid substrate tank has been filled with the liquid substrate, said at least one extraction probe being adjustable in height and being led in a gas-tight and height-adjustable manner through said skirt into said tank interior space.

20. The liquid substrate tank according to claim 1, which further comprises:
a shut-off element being separately actuable by said regulating or control device;
said at least one extraction line being formed by at least one extraction probe being inserted into said tank interior space and being led in said tank interior space as far as into a vicinity of said at least one extraction channel;
said at least one extraction probe including extraction probes associated with different extraction channels; and
said extraction probes associated with different extraction channels or each of said extraction probes being opened and shut off by said shut-off element.

21. The liquid substrate tank according to claim 1, wherein said receiving or sedimentation tank is a separator, and at least one recirculation line is led from said separator to the liquid substrate tank.

* * * * *